United States Patent
Fotinos

[11] Patent Number: 5,925,373
[45] Date of Patent: Jul. 20, 1999

[54] TRANSDERMAL DELIVERY DEVICE CONTAINING AN ESTROGEN

[75] Inventor: Spiros A. Fotinos, Kolonaki, Greece

[73] Assignee: Lavipharm S.A., Peania Attica, Greece

[21] Appl. No.: 08/619,642

[22] PCT Filed: Jul. 25, 1995

[86] PCT No.: PCT/EP95/02938

§ 371 Date: Jun. 19, 1996

§ 102(e) Date: Jun. 19, 1996

[87] PCT Pub. No.: WO96/03119

PCT Pub. Date: Feb. 8, 1996

[30] Foreign Application Priority Data

Jul. 26, 1995 [GR] Greece ............................. 940100369

[51] Int. Cl.⁶ .................................................... A61F 13/00
[52] U.S. Cl. .......................................... 424/449; 424/448
[58] Field of Search ..................... 424/449, 448

[56] References Cited

U.S. PATENT DOCUMENTS

| | | | |
|---|---|---|---|
| 4,906,475 | 3/1990 | Kim | 424/449 |
| 5,154,922 | 10/1992 | Govil et al. | 424/448 |
| 5,223,261 | 6/1993 | Nelson et al. | 424/443 |
| 5,252,334 | 10/1993 | Chiang et al. | 424/448 |
| 5,262,165 | 11/1993 | Govil et al. | 424/448 |
| 5,362,497 | 11/1994 | Yamada | 424/449 |
| 5,372,819 | 12/1994 | Godbey | 424/449 |
| 5,518,734 | 5/1996 | Stefano et al. | 424/448 |
| 5,629,019 | 5/1997 | Lee | 424/489 |
| 5,705,185 | 1/1998 | Stefano et al. | 424/448 |

FOREIGN PATENT DOCUMENTS

| | | | |
|---|---|---|---|
| 0 328 806 A2 | 8/1989 | European Pat. Off. | A61K 9/70 |
| 0 416 842 A1 | 3/1991 | European Pat. Off. | A61L 15/44 |
| 0 430 491 A2 | 6/1991 | European Pat. Off. | A61L 15/16 |
| 0 463 454 A2 | 1/1992 | European Pat. Off. | A61L 15/16 |
| 0 483 370 A1 | 5/1992 | European Pat. Off. | A61L 31/565 |
| 0 430 491 B1 | 6/1994 | European Pat. Off. | A61L 15/16 |
| 0 402 407 B1 | 8/1994 | European Pat. Off. | A61L 15/16 |
| 0 622 075 A1 | 11/1994 | European Pat. Off. | A61K 9/70 |
| 0 614 356 B1 | 9/1995 | European Pat. Off. | A61K 9/70 |
| 43 36 557 A1 | 10/1993 | Germany | A61L 15/44 |
| 90/06736 | 6/1990 | WIPO | A61F 13/02 |
| 91/05529 | 5/1991 | WIPO | A61F 13/00 |
| 92/07590 | 5/1992 | WIPO | A61L 15/16 |
| 92/10231 | 6/1992 | WIPO | A61M 37/00 |

*Primary Examiner*—D. Gabrielle Brouillette
*Attorney, Agent, or Firm*—Bromberg & Sunstein LLP

[57] ABSTRACT

A composition for use in a three layer transdermal delivery system is disclosed, the composition comprising an adhesive matrix having sufficient strength to maintain an association on the skin for at least 3 days. The adhesive matrix contains the flux enhancer linoleic acid, an anti-oxidant and an effective dose of one or more steroid hormones with female sex related activity.

30 Claims, 9 Drawing Sheets

MODIFIED FRANZ DIFFUSION CELL

TRANSDERMAL DELIVERY DEVICE CONTAINING AN ESTROGEN

This application is a 371 of PCT/EP95/02938, filed Jul. 25, 1995.

The present invention relates to a device for the administration of estradiol alone or in combination with progestin (s), encompassing a specific enhancer that achieves elevated transdermal fluxes and optionally an anti-oxidant that achieves better product stability and to a method for manufacturing such device.

17β-estradiol is the main estrogen produced by the ovaries in pre-menopausal women (J. A. Balfur and R. C. Heel, Drugs 40 4, 561–582, 1990).

17β-estradiol, the naturally occurring estrogen, has mainly been used in two areas, such as fertility control and estrogen replacement therapy.

Oral administration of estradiol results in an almost complete degradation of this hormone in the digestive tract, due to the phenomenon of first-pass hepatic metabolism. Since a large amount of the administered estradiol, approximately 90%, is destroyed, a large excess should be administered in order to achieve an effective therapeutic result.

It is well-known, that oral administration of estradiol is associated with a number of major side effects such as thrombophlebitis and thrombosis, pulmonary embolism, coronary thrombosis, myocardial infraction, cerebral thrombosis, cerebral hemorrhage and hypertension.

Estrogen replacement therapy is a special need for females on menopause or oophorectomy (loss of one or both ovaries by surgery) and/or pituitary failure. It can also contribute to osteoporosis (loss of bone mass) and atherosclerosis.

Administration of estradiol to post-menopausal women has been found to make post-menopausal symptoms (hot flushes, sweating, nervousness, sleep disturbance) less intense.

Co-administration of progestin has been shown to be advantageous for eliminating the side-effects caused by the administration of estradiol itself. Thus, in both fertility control and estrogen replacement therapy, the available therapeutic dosage schemes contain an effective amount of progestin. (Y. W. Chien, T-Y. Chien and Y-C. Huang, U.S Pat. No. 4,906,169 (transdermal Estrogen/Progestin Dosage Unit, System and Process), Mar. 6, 1990.

It has been of great importance to develop a delivery system which will provide certain advantages such as minimization of side effects, prolonged and controlled rate of administration of the hormones, rapid termination of the treatment, and improvement of patient compliance.

The introduction of transdermal systems was found to satisfy the above requirements, which, thus, permits the use of the natural estrogen, 17β-estradiol, and the use of lower daily doses with the same efficacy because of reduced first-pass hepatic metabolism and continuous drug input.

A number of transdermal delivery systems of various designs exist. They are in general well tolerated, with only 2.5–7% of patients overall having been reported to discontinue the use of transdermal delivery due to severe irritation problems.

The most frequent problem relates to insufficient adhesion of the transdermal "patch" to the skin during wear, resulting in patch loss. Typically, estradiol delivery systems are designed to be worn and to deliver the drug for 3–4 days.

Several sizes of transdermal estradiol patches already exist on the market, for example patches having a surface area of, 5, 10, 16 and 20 cm$^2$ containing 2, 4, 3.2 and 8 mg of estradiol respectively; the drug is delivered at a rate of 0.21 μg/cm$^2$/hr corresponding to delivery rates of 0.025, 0.05, 0.08 and 0.1 mg per 24 hours (for up to 4 days).

A number of patented systems exist for the delivery of estradiol through the skin, wherein, some selectively presented, (e.g.—Chien, Yie., W. and Chien, Te-Yen, WO 87/07138, Transdermal Absorption Dosage Unit For Estradiol and other Estrogenic Steroids and Process for Administration—Transdermal drug delivery device using a polymer-filled microporous membrane to achieve delayed onset, by Venkatraman S., Cygnus Therapeutic Systems WO 93/03693—Solid matrix system for transdermal drug delivery, by Chia-Ming Chiang et al, Cygnus Therapeutic Systems, U.S. Pat. No. 5,252,334 (Dec. 10, 1993)—Estradiol transdermal delivery system, by Kim B. et al., Paco Pharmaceutical Services, U.S. Pat. No. 4,906,475/Jun. 3, 1990—Transdermal estrogen/progestin dosage unit, system and process, by Chien Y. et al., Rutgers, the State University of New Jersey, WO 90/06736).

There are basically two types of transdermal drug delivery systems:

a) Liquid reservoir
   Drug impermeable covering 1.
   Drug formulation reservoir 2.
   Rate-controlling membrane 3.
   Adhesion layer 4.
   Release liner 5.
(as illustrated in FIG. 1)

In this case, estradiol is formulated in a liquid medium and the drug is released from the system via a polymeric membrane.

b) Matrix
   Occlusive cover sheet 6.
   Adhesive matrix drug reservoir 7.
   Release liner 8.
(as illustrated in FIG. 2)

In this type of system the drug is formulated directly in the adhesive used which is placed directly in contact with the skin.

In general, matrix transdermal delivery system enjoy better patient acceptance, because they are considered to be more convenient than liquid reservoir systems. Furthermore, liquid patches developed for estradiol usually exhibit interactions between the adhesive substance and the semi-solid components of the liquid-reservoir, leading to reduced-adhesiveness and altered skin flux rates.

All the available enhancers could influence the physicochemical properties of a final transdermal delivery system, such as adhesion, plasticity etc. In general, the selection of all the ingredients for a transdermal delivery system is guided by the desired physicochemical properties.

In the present invention, a percentage concentration range of the enhancer is proposed, while an optimum concentration, satisfying our needs for the desirable "patch" with the appropriate skin flux adhesion and removal properties, has been identified.

In this invention, linoleic acid is used as skin permeation enhancer. This unsaturated aliphatic acid alone or in combination has been for years in many topical formulations such as cosmetics, toiletries, etc.

It is an object of this invention to provide an improved transdermal estradiol delivery system suitable for use in women on fertility control and estrogen replacement therapy which overcomes the problems of the prior art systems.

According to a first aspect of the present invention there is provided a composition for use in a transdermal drug delivery system comprising:

(a) an adhesive;

(b) an estrogen; and (c) a flux enhancer.

Preferably, the adhesive is at least one acrylic adhesive.

Preferably, the adhesive is a mixture of two acrylic adhesives.

Preferably, the two acrylic adhesives are in a dry weight ratio of about 80% to about 20% respectively.

Preferably, the amount of estrogen is from about 0.1 to about 8% w/w.

Preferably, the amount of estrogen is 2% w/w.

Preferably, the estrogen is 17-β estradiol, ethinyl-estradiol or combinations thereof.

Preferably, the preceding claims wherein the amount of flux enhancer is from about 0.1 to about 20%.

Preferably, the amount of flux enhancer is about 5%.

Preferably, the flux enhancer is linoleic acid.

Preferably, the estrogen is combined with a progestin.

Preferably, the amount of progestin is from about 0.1 to about 10% w/w.

Preferably, the amount of progestin is about 4% w/w.

Preferably, the progestin is norethindrone acetate, levonorgestrel or medroxyprogesterone.

Preferably, the preceding claims further comprising an antioxidant.

Preferably, the antioxidant is butylhydroxytoluene (BHT).

Preferably, there are a plurality of compositions.

Preferably, each of the compositions contains different concentrations of adhesive, estrogen and flux enhancer.

According to a second aspect of the present invention, there is provided a transdermal delivery system comprising an adhesive, an estrogen, and a flux enhancer.

Preferably, a part of the adhesive is in contact with a polymeric release liner which seals and protects the adhesive during storage, and wherein the liner is capable of being peeled off and discarded prior to use of the transdermal delivery system.

Preferably, the release liner is of either polymeric or paper origin.

Preferably, at least a part of the adhesive is in contact with a backing layer which is substantially impermeable to the components of the composition the backing layer being occlusive or breathable.

Preferably, the controlled delivery of estrogen over a period of 1 to 11 days.

According to a third aspect of the present invention there is provided a method of administering estrogen through the skin by use of a transdermal delivery system, the delivery system comprising an adhesive, an an estrogen; and a flux enhancer.

BRIEF DESCRIPTION OF THE DRAWINGS

Embodiments of the present invention will now be described by way of example with reference to the drawings in which.

It is an advantage of this invention to provide a transdermal delivery system which sufficiently delivers in vivo estrogen alone, or in combination with progestin, through intact skin at a controlled rate for 1–11 days.

It is another advantage of this invention to provide a transdermal estrogen and estrogen/progestin combination through a patch that is of smaller size for the same dose than other patches developed to date.

It is another advantage of this invention to provide a transdermal delivery system for administration of estrogen or in combination with progestin with better stability characteristics than other developed patches.

The present invention is also advantageous in that it relates to the use of linoleic acid together with an anti-oxidant, which enhances the rate of estradiol permeation and maintains superior product stability, that is innovative and unique as well.

This invention offers a simple and effective means of delivering estrogen, preferably estradiol and estrogen/progestin combinations through the skin. The hormones are formulated with a mixture of dermatologically acceptable acrylic adhesives, a flux enhancer preferably linoleic acid and optionally an anti-oxidant compound.

Figure 1:
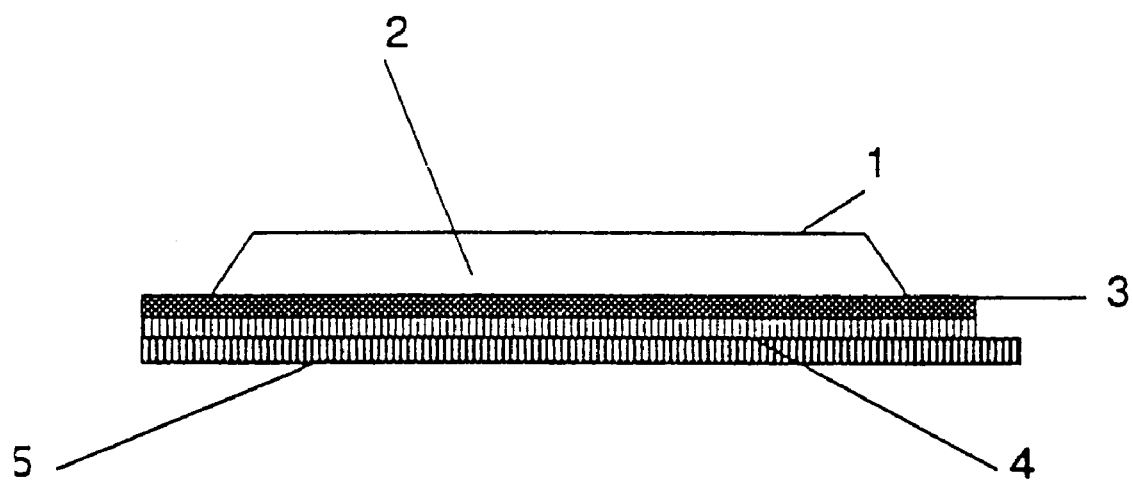
FIG. 1 is a transdermal delivery system having a liquid reservoir.
Figure 2:
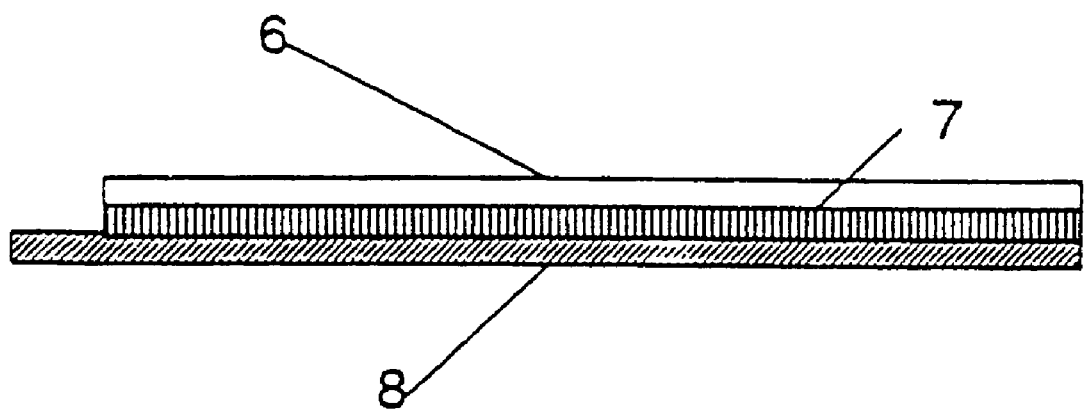
FIG. 2 is a transdermal delivery system having a matrix.
Figure 3:
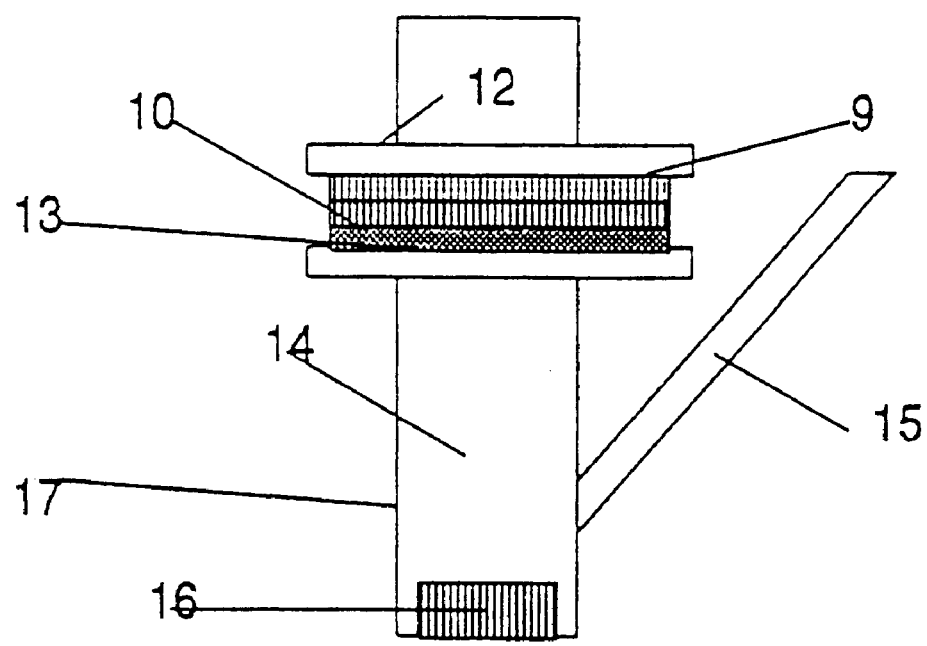
FIG. 3 is a modified Franz Diffusion cell.

The transdermal estradiol or estradiol/progestin delivery systems (illustrated in FIG. 3) of this invention comprise:

a) a backing layer 9, which is substantially impermeable to the estradiol and progestin(s) to be delivered transdermally;

b) an adhesive matrix 10, which is in contact with said backing layer and has distributed therein an effective amount of estradiol or estradiol/progestin combinations with an enhancing agent such as linoleic acid and an anti-oxidant compound, such as butylhydroxytoluene (BHT) and which secures the dosage unit in contact with the skin of the subject being treated for a period of 1–11 days to permit the hormones to be absorbed transdermally at a controlled rate; and c) a release liner 11, which is in contact with said adhesive matrix and which is stripped from the unit prior to the use.

The backing layer can be made of any suitable material which is impermeable to the estradiol alone or in combination with progestin(s) which are dissolved or otherwise distributed in the adhesive matrix. Preferably the materials for making the backing layer are commercially available films of Saranex sold by Dow Chemicals or of polyethylene sold by 3M, providing thus the desirable properties in the adhesive matrix.

The adhesive layer must be made of materials biologically acceptable and compatible with said hormones and the skin permeation enhancer. In this invention, preferably a pressure-sensitive material is used such as the vinyl acetate-acrylate multipolymer of Gelva 737 and/or Gelva 788 resin solution sold by Monsanto.

The adhesive layer is then covered with release liner which is made of materials impermeable to the hormones, the skin permeation enhancer and any other components of the dosage unit, and which is easily stripped or released prior the use. Preferably the release liner is made of siliconized polyester substance sold by release Release Technologies.

Skin permeation enhancers, which can be employed for carrying out this invention, can widely vary. Specific skin permeation enhancers are distributed within the adhesive matrix and result in a good absorption of the hormones.

The above formulation description can be presented in the following tables which demonstrate the composition of a transdermal delivery unit consisting of (a) a single adhesive substance and (b) a mixture of adhesives.

TABLE 1

Single Adhesive Formulation

| COMPONENT | QUALITY | QUANTITY % w/w (on a dry basis) |
|---|---|---|
| 17β-estradiol | Pharmaceutically pure | 2.0 |
| Gelva 737 | Multipolymer Solution | 92.9 |
| Pamolyn 200 | 77% min linoleic acid | 5.0 |
| Butyl Hydroxy Toluene (BHT) | | 0.1 |

TABLE 2

Mixed Adhesive Formulation

| COMPONENT | QUALITY | QUANTITY % w/w (on a dry basis) |
|---|---|---|
| 17β-estradiol | Pharmaceutically pure | 2.0 |
| Gelva 737/788 (80/20 ratio by weight in a dried coating) | Multipolymer Solution | 92.9 |
| Linoleic acid | >96% | 5.0 |
| Butyl Hydroxy Toluene (BHT) | | 0.1 |

This invention is illustrated further by the following examples. Examples are not to be seen as limiting the scope of invention.

EXAMPLE 1

Preparation of Adhesive Mixture and Transdermal Delivery Device

The following ingredients are used in preparing the hormone containing adhesive matrix: estradiol, Gelva, linoleic acid and butylhydroxytoluene (BHT).

To 75 g of adhesive (Gelva 737 with a total solids content of about 33.8%) solution in toluene ethylacetate and ethanol, estradiol (0.5 g) and linoleic acid (1.25 g) are added. 200 μl of BHT solution in isopropanol (0.6 g BHT per 100 ml of isopropanol) are added and the mixture is stirred at room temperature until all estradiol is dissolved. When a mixture of adhesives is used, it consists of 60.5 gl Gelva 737 and 11.0 gl Gelva 788.

The adhesive mixture is formulated in a transdermal system as follows: Using an appropriate coating device such as 15 mil casting knives, a layer of the adhesive mixture is coated onto the silicone treated side of polyethylene sheet. The coating is dried in an oven at 70° C. for 15 minutes and it is then laminated with a polyester layer on the corona-treated (roughened) side. The process ends with cutting the multi-layer laminate to shapes of the desired geometry and size.

EXAMPLE 2

Permeability of the Transdermal Delivery Device

The dosage units obtained, as described in the Example 1, are evaluated. The transdermal absorption (flux) of estradiol from the adhesive matrix of this invention is determined in vitro by using human cadaver skin, according to the procedure described by Franz T., In Percutaneous absorption on the relevance of in vitro data, J. Invest. Derm. 64, 190–195, 1975.

Figure 4:
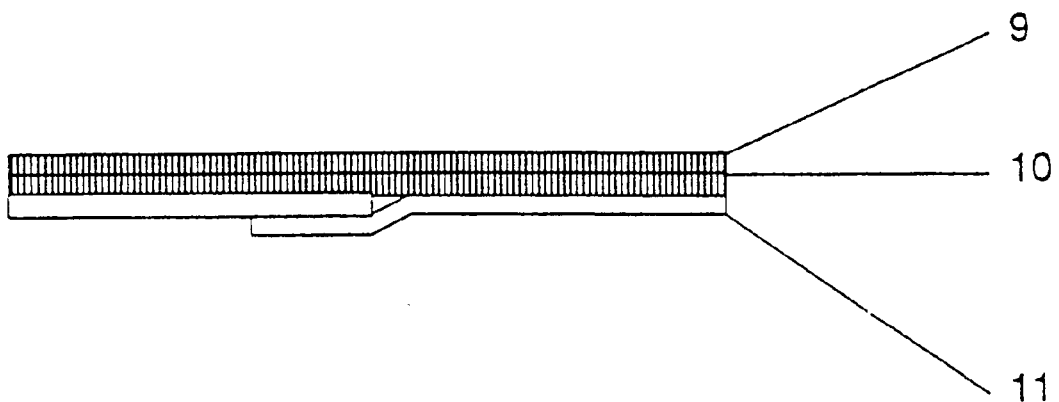
FIG. 4 is a transdermal delivery system according to the present invention.

A typical experimental setup for flux measurements (modified Franz diffusion cell), illustrated in FIG. 4, comprises a) Glass lid 12, b) Backing sheet 9, C) Drug in the adhesive matrix 10, d) Skin 13, e) Receiving medium 14, f) Sampling arm 15, g) Stirrer 16, h) Receiver compartment 17 and i) Clamp (not shown).

For in vitro flux studies, the stratum corneum of human cadaver skin was used. Using fresh, post-mortem skin samples, the stratum corneum was separated from the skin by the technique described by Kligman, A. M. and Christophers, E., in Preparation of isolated sheets of human stratum corneum. Arch. Derm., 88, 702, 1963.

The stratum corneum and the transdermal system of the Example 1 were cut into approximately 2–3 cm$^2$ squares. A sample of stratum corneum was placed onto the flat surface of the flux cell. After removing the release liner from the transdermal system, the adhesive matrix was laminated onto the stratum corneum, the whole was covered by a glass lid, and secured by a clamp.

The receiver medium was a 0.02 wt. % aqueous solution of sodium azide. The assembled cells were placed in a circulating water bath calibrated to maintain the skin surface temperature at 32±1° C.

At predetermined time intervals of 6, 12, 24, 36, 48, and 72 hours, the entire content of the receiver was collected for the quantitative determination of estradiol, employing an HPLC method adapted from T. Loftsson and N. Bodor, Acta Pharm. Nord., 1, 4, 1989.

The receiver was then again filled with fresh receiving medium. Special care was taken to avoid accumulation of air bubbles at the skin/solution interface.

The cumulative amount of estradiol ($Q_t$=μg.cm$^{-2}$) permeated per unit of area at any time (t) is calculated by using the following formula.

$$Q_t = \Sigma^t_{n=0}(C_n V)/A$$

where $C_n$ is the concentration (μg/ml) of the drug in the receiving medium for each sampling time, V is the volume (6.3 ml) of receiver solution, and A is the cell's diffusional area (0.636 cm$^2$).

Figure 5:
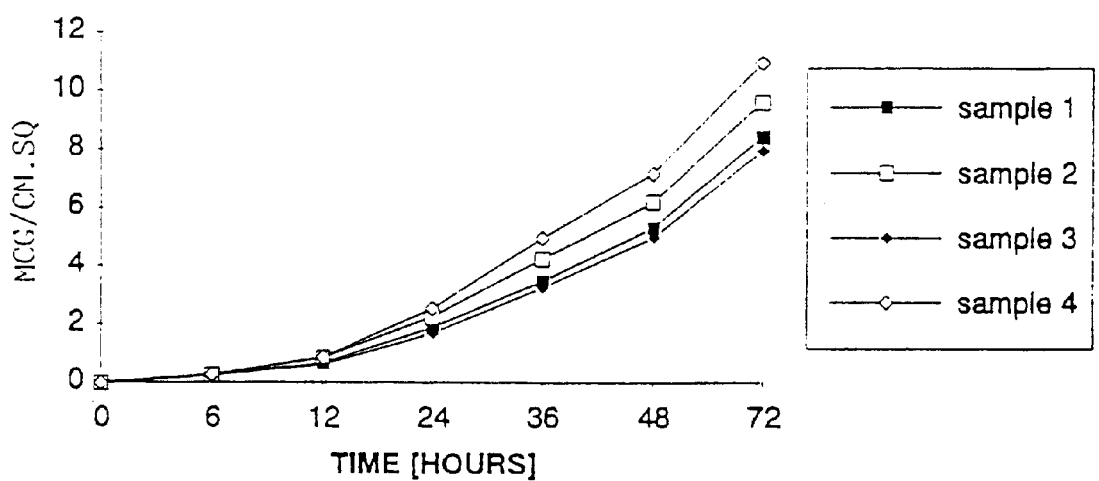
FIG. 5 is a graph showing the flux of estradiol through human stratum corneum in vitro.

Typical results are shown in the graph of FIG. 5.

Figure 6:
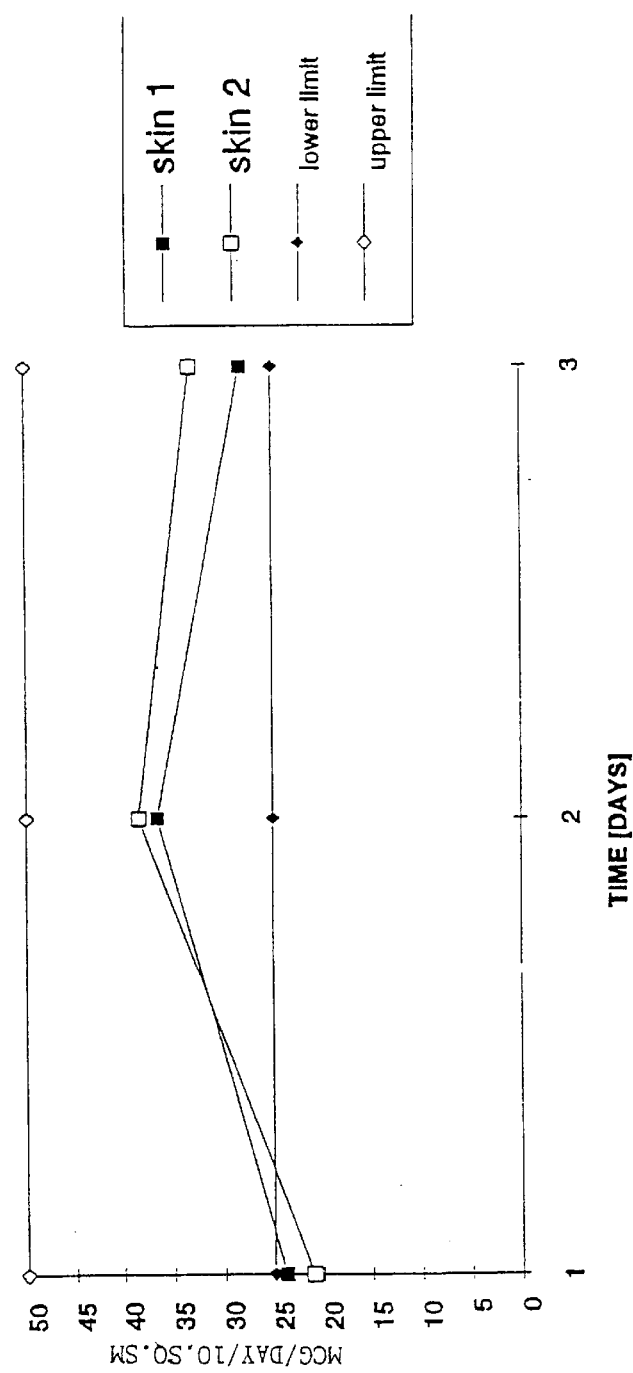
FIG. 6 is a graph showing the permeation of estradiol per day from a 10 sq. cm patch.

The flux of estradiol released from a transdermal delivery system of a given size can be calculated using the above data. The results obtained are given in the graph of FIG. 6.

A comparative study of skin flux determination between estradiol transdermal system described in the Example 1 and SYSTEN 50 Lot 3A01AZ (a matrix patch introduced by Johnson and Johnson) is presented in the following Table:

TABLE 3

Competitive skin flux studies between Estradiol transdermal system and SYSTEN 50

| Transdermal system | Cumulative fluxes ($\mu g/cm^2$) | | | Incremental fluxes ($\mu g/cm^2$) ratio (sample to reference) | | | |
|---|---|---|---|---|---|---|---|
| | (0–24 h) | (0–48 h) | (0–72 h) | (0–24 h) | (24–48 h) | (48–72 h) | Average |
| Estradiol | 2.11 | 5.04 | 7.83 | 2.11 / 1.10 | 2.93 / 1.87 | 2.79 / 2.05 | 2.61 / 1.67 |
| SYSTEN 50 | 1.92 | 3.49 | 4.85 | 1.92 / 1.00 | 1.57 / 1.00 | 1.36 / 1.00 | 1.62 / 1.00 |

The results from the Table 3 indicate that the estradiol transdermal delivery system of the present invention exhibits elevated skin fluxes comparing to that of SYSTEN 50. As skin flux rates are the primary parameter of performance of a transdermal delivery system, the rates of the above table clearly indicate that the transdermal delivery system described in this invention, can be of a smaller size that the commercially available. A smaller size "patch" signifies: 1) a smaller occluded area, therefore less risk of irritation, 2) better aesthetics and therefore, convenience, acceptability and compliance by patients under treatment, and 3) higher production output.

EXAMPLE 3

Stability of the Transdermal Delivery Device

The dosage units described in the Example 1 are evaluated.

Figure 7:
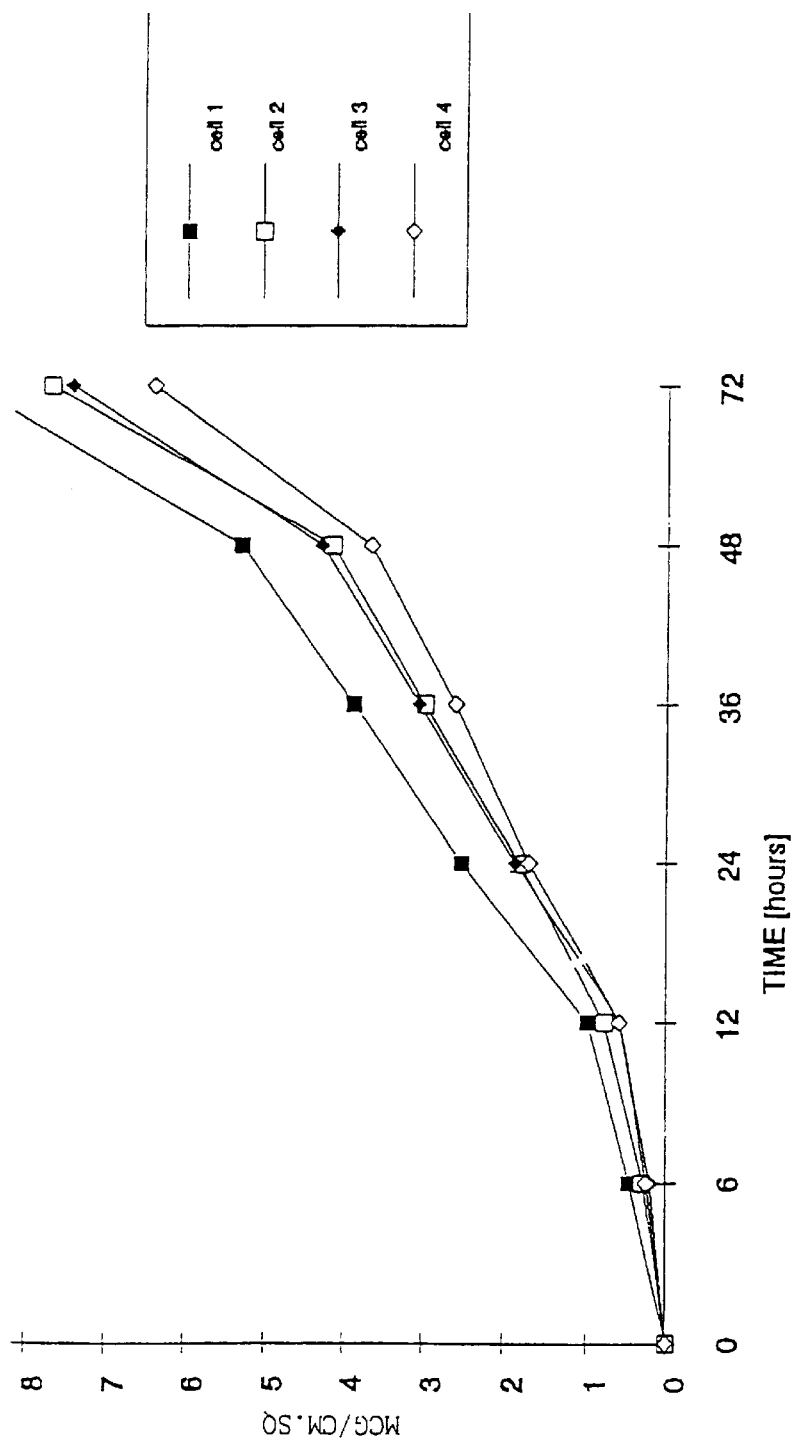
FIG. 7 is a graph showing the flux of estradiol through human stratum corneum in vitro (after storage for 8 weeks at room temperature).

The stability of estradiol in the adhesive matrix is determined by measuring fluxes of estradiol from the formulation at various intervals during storage of the transdermal systems. The graph of FIG. 7 showing the results obtained after 8 weeks at room temperature, indicates that little change in the product's performance occurred during this period.

The stability of the transdermal system can also be evaluated by measuring the release rate of estradiol from the matrix employing a standard drug release test (U.S. Pharmacopeia XXII, p. 1581).

Figure 8:
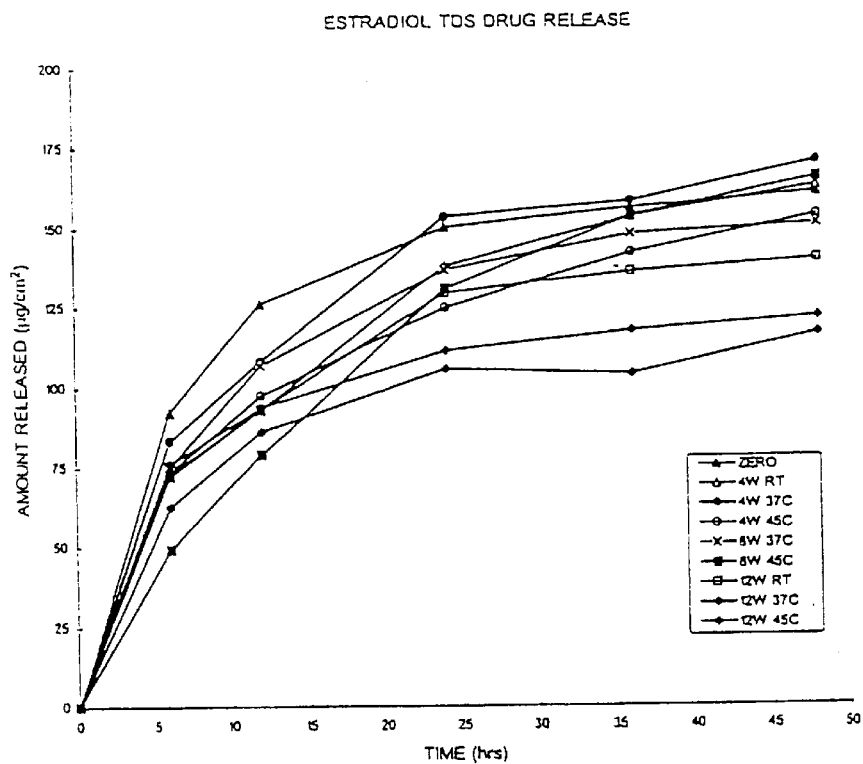
FIG. 8 is a graph showing estradiol TDS drug release.

The results of such measurements are given in the graph of FIG. 8.

Samples of the transdermal system were kept at room temperature and at 37° C. and 45° C. for up to 12 weeks, (see also graph of FIG. 8). The results again indicate that the system's performance remains satisfactory under these conditions.

EXAMPLE 4

The Effect of Enhancer on the Flux of Estradiol Through Human Cadaver Skin

The transdermal units described in the Example 1 are evaluated. Various combinations of estradiol and linoleic acid amounts were tested to establish an optimum ratio of the drug and enhancer. The following examples, presented in the table below, illustrate the effect of various concentrations of the two components on the flux of estradiol through human cadaver skin.

TABLE 4

Effect of linoleic acid on estradiol flux

| | Flux in $\mu g/cm^2/hr$ | |
|---|---|---|
| Transdermal delivery device | 24 | 48 |
| A. | | |
| 4% estradiol & 2% linoleic acid | 0.073 | 0.072 |
| 4% estradiol & 5% linoleic acid | 0.076 | 0.080 |
| B. | | |
| 3% estradiol & 5% linoleic acid | 0.133 | 0.138 |
| Estraderm ® Control | 0.067 | 0.079 |
| 1.5% estradiol & 5% linoleic acid | 0.090 | 0.100 |
| D. | | |
| 2% estradiol & 5% linoleic acid | 0.120 | 0.130 |
| Estraderm ® Control | 0.060 | 0.110 |

As it is indicated above, various estradiol/linoleic acid combinations result in various flux rates.

Differences occurred in experimental results are mostly based upon the skin donor(s).

EXAMPLE 5

Skin Irritation and Sensitisation Studies Using Estradiol Transdermal System

The transdermal units described in the Example 1 are tested.

A skin irritation study was conducted in six healthy rabbits of the New Zealand white variety.

The back and flanks of each animal are clipped free of fur with an electric clipper 12 hours before testing. Just prior to test article application, each rabbit receives four parallel epidermal abrasions with a sterile needle at one test site (left flank), while the skin at the opposite site remains intact.

A 5 $cm^2$ patch of the test article and a 5 $cm^2$ patch of the control article are then applied to each site (four sites per rabbit) to an area of skin approximately 2.7×3.7 cm. The patches are covered with a non-reactive tape. The trunk of each animal is wrapped with a binder.

After 96 hour exposure, the binders, tape, and patches are removed. The test sites are gently sponged with deionized water to remove any residue of test article. After at least 30 minutes, the sites are inspected and scored. Another evaluation is also conducted at 144 hours after application.

Each test site is examined for dermal reactions using the Draize scoring criteria. The primary irritation index of the test article is calculated following test completion. A substance with an empirical score of less than 5 would not be considered a primary irritant to the skin.

The primary irritation index of the test article (estradiol transdermal system of this invention) and of the control article (Estraderm$^R$TTS 25 μg/24 h. Lot # 176700, expiration date 05/94) are calculated to be 1.70 and 1.75, respectively.

Individual experimental results are given in the following Table. The results for the test article of this invention are given first, followed (after /) by the results for control article.

The table that follows presents the data for each rabbit.

TABLE 5

Skin irritation test

| Rabbit No. | Reaction | 96 hours Intact | 96 hours Abraded | 144 hours Intact | 144 hours Abraded |
|---|---|---|---|---|---|
| No 1 | Erythema: | 2/0 | 2/0 | 1/0 | 0/1 |
|  | Oedema: | 1/0 | 1/1 | 1/0 | 0/1 |
| No 2 | Erythema: | 0/0 | 0/0 | 0/0 | 0/0 |
|  | Oedema: | 0/0 | 0/0 | 0/0 | 0/0 |
| No 3 | Erythema: | 1/2 | 1/1 | 1/1 | 1/1 |
|  | Oedema: | 0/1 | 1/1 | 1/1 | 2/1 |
| No 4 | Erythema: | 0/0 | 0/0 | 1/1 | 0/1 |
|  | Oedema: | 0/0 | 0/0 | 1/0 | 0/1 |
| No 5 | Eythema: | 1/1 | 2/2 | 0/1 | 1/2 |
|  | Oedema: | 0/1 | 2/2 | 0/1 | 2/2 |
| No 6 | Erythema: | 3/1 | 2/2 | 1/3 | 2/2 |
|  | Oedema: | 2/1 | 2/2 | 1/1 | 2/2 |

Under the conditions of this test, the transdermal system tested could not be considered a primary skin irritant, since the primary irritation index was less than 5 and the difference between the test and control scores was not significant.

A skin sensitisation study was conducted in 35 healthy albino guinea pig of the Hartley strain to evaluate and compare the dermal sensitisation potential of estradiol transdermal system and Estraderm TTS patch, according to the method described by Buehler in Archives of Derm. 91, 171, 1965.

The estradiol transdermal system was occlusively patched to ten guinea pigs and the control patch was occlusively patched to ten guinea pigs, three times a week until nine induction applications were conducted. Similarly, five positive control guinea pigs were occlusively patched twice a week, with a 0.1% solution of 1-chloro-2,4-dinitrobenzene (DNCB) in propylene glycol, until six inductions had been completed. Following a recovery period of three weeks, the original ten tests and ten controls, ten previously untreated negative control animals and the five positive control animals received a challenge patch. All sites were scored at 24, 48, and 72 hours after challenge patch removal.

The results obtained are shown in the following Tables 6 and 7. Specifically the results referred to the induction of dermal reactions and challenge phase for the test article of this invention are given first, followed (after /) by the results for the control article.

TABLE 6

Skin sensitisation test: Dermal reactions - induction phase

| Animal Number | OBS | \multicolumn{9}{c}{Dermal Reaction The Day After Patch Removal} |
|---|---|---|---|---|---|---|---|---|---|---|

| Animal Number | OBS | 1 | 2 | 3 | 4 | 5 | 6 | 7 | 8 | 9 |
|---|---|---|---|---|---|---|---|---|---|---|
| 1/11 | ER | 0/0 | 0/0 | 0/0 | 0/0 | 0/0 | 0/0 | 0/0 | 0/0 | 0/0 |
|  | OED | 0/0 | 0/0 | 0/0 | 0/0 | 0/0 | 0/0 | 0/0 | 0/0 | 0/0 |
| 2/12 | ER | 0/0 | 0/0 | 0/0 | 0/0 | 0/0 | 0/0 | 0/0 | 0/0 | 0/1 |
|  | OED | 0/0 | 0/0 | 0/0 | 0/0 | 0/0 | 0/0 | 0/0 | 0/0 | 0/1 |
| 3/13 | ER | 0/0 | 0/0 | 0/0 | 0/0 | 0/0 | 0/0 | 0/0 | 0/0 | 0*/0 |
|  | OED | 0/0 | 0/0 | 0/0 | 0/0 | 0/0 | 0/0 | 0/0 | 0/0 | 0/0 |
| 4/14 | ER | 0/0 | 0/0 | 0/0 | 0/0 | 0/0 | 0/0 | 0/0 | 0/0 | 0/0 |
|  | OED | 0/0 | 0/0 | 0/0 | 0/0 | 0/0 | 0/0 | 0/0 | 0/0 | 0/0 |
| 5/15 | ER | 0/0 | 0/0 | 0/0 | 0/0 | 0/0 | 0/0 | 0/0 | 0/0 | 0*/0 |
|  | OED | 0/0 | 0/0 | 0/0 | 0/0 | 0/0 | 0/0 | 0/0 | 0/0 | 0/0 |
| 6/16 | ER | 0/0 | 0/0 | 0/0 | 0/0 | 0/0 | 0/0 | 0/0 | 0/0 | 0*/0 |
|  | OED | 0/0 | 0/0 | 0/0 | 0/0 | 0/0 | 0/0 | 0/0 | 0/0 | 0/0 |
| 7/17 | ER | 0/0 | 0/0 | 0/0 | 0/0 | 0/0 | 0/0 | 0/0 | 0/0 | 0/0 |
|  | OED | 0/0 | 0/0 | 0/0 | 0/0 | 0/0 | 0/0 | 0/0 | 0/0 | 0/0 |
| 8/18 | ER | 0/0 | 0/0 | 0/0 | 0/0 | 0/0 | 0/0 | 0/0 | 0/0 | 0/0 |
|  | OED | 0/0 | 0/0 | 0/0 | 0/0 | 0/0 | 0/0 | 0/0 | 0/0 | 0/0 |
| 9/19 | ER | 0/0 | 0/0 | 0/0 | 0/0 | 0/0 | 0/0 | 0/0 | 0/0 | 0/0 |
|  | OED | 0/0 | 0/0 | 0/0 | 0/0 | 0/0 | 0/0 | 0/0 | 0/0 | 0/0 |
| 10/20 | ER | 0/0 | 0/0 | 0/0 | 0/0 | 0/0 | 0/0 | 0/0 | 0/0 | 0/0 |
|  | OED | 0/0 | 0/0 | 0/0 | 0/0 | 0/0 | 0/0 | 0/0 | 0/0 | 0/0 |

ER: ERYTHEMA
OED: OEDEMA
*: BALDNESS

TABLE 7

Skin sensitisation test: Challenge phase

| Animal Number | OBS | \multicolumn{3}{c}{Hours After Patch Application} |
|---|---|---|---|---|

| Animal Number | OBS | 24 | 48 | 72 |
|---|---|---|---|---|
| 1/11 | ER | 0/0 | 0/0 | 0/0 |
|  | OED | 0/0 | 0/0 | 0/0 |
| 2/12 | ER | 0/0 | 0/0 | 0/0 |
|  | OED | 0/0 | 0/0 | 0/0 |
| 3/13 | ER | 0/0 | 0/0 | 0/0 |
|  | OED | 0/0 | 0/0 | 0/0 |
| 4/14 | ER | 0/0 | 0/0 | 0/0 |
|  | OED | 0/0 | 0/0 | 0/0 |
| 5/15 | ER | 0/0 | 0/0 | 0/0 |
|  | OED | 0/0 | 0/0 | 0/0 |
| 6/16 | ER | 0/0 | 0/0 | 0/0 |
|  | OED | 0/0 | 0/0 | 0/0 |
| 7/17 | ER | 0/1 | 0/0 | 0/0 |
|  | OED | 0/1 | 0/0 | 0/0 |
| 8/18 | ER | 0/0 | 0/0 | 0/0 |
|  | OED | 0/0 | 0/0 | 0/0 |
| 9/19 | ER | 0/0 | 0/0 | 0/0 |
|  | OED | 0/0 | 0/0 | 0/0 |
| 10/20 | ER | 0/0 | 0/0 | 0/0 |
|  | OED | 0/0 | 0/0 | 0/0 |

ER: ERYTHEMA
OED: OEDEMA

The following Table presents the results obtained during challenge phase in the negative control animals.

TABLE 8

Skin sensitisation test: Challenge phase (Negative control)

| Animal Number | OBS | A | B | A | B | A | B |
|---|---|---|---|---|---|---|---|
| 26 | ER | 0 | 0 | 0 | 0 | 0 | 0 |
|  | OED | 0 | 0 | 0 | 0 | 0 | 0 |
| 27 | ER | 1 | 1 | 1 | 1 | 0 | 0 |

TABLE 8-continued

Skin sensitisation test: Challenge phase (Negative control)

| Animal Number | OBS | A | B | A | B | A | B |
|---|---|---|---|---|---|---|---|
|  | OED | 0 | 0 | 0 | 0 | 0 | 0 |
| 28 | ER | 0 | 0 | 0 | 0 | 0 | 0 |
|  | OED | 0 | 0 | 0 | 0 | 0 | 0 |
| 29 | ER | 0 | 0 | 0 | 0 | 0 | 0 |
|  | OED | 0 | 0 | 0 | 0 | 0 | 0 |
| 30 | ER | 0 | 0 | 0 | 0 | 0 | 0 |
|  | OED | 0 | 0 | 0 | 0 | 0 | 0 |
| 31 | ER | 0 | 0 | 0 | 0 | 0 | 0 |
|  | OED | 0 | 0 | 0 | 0 | 0 | 0 |
| 32 | ER | 0 | 0 | 0 | 0 | 0 | 0 |
|  | OED | 0 | 0 | 0 | 0 | 0 | 0 |
| 33 | ER | 0 | 0 | 0 | 0 | 0 | 0 |
|  | OED | 0 | 0 | 0 | 0 | 0 | 0 |
| 34 | ER | 1 | 1 | 1 | 1 | 0 | 0 |
|  | OED | 1 | 1 | 0 | 0 | 0 | 0 |
| 35 | ER | 0 | 0 | 0 | 0 | 0 | 0 |
|  | OED | 0 | 0 | 0 | 0 | 0 | 0 |

ER: ERYTHEMA
OED: OEDEMA
A = Estraderm TTS Patch (Left Flank)
B = Estradiol Transdermal Patch (Right Flank)

The results of the positive control animals obtained from induction and challenge phase are presented below.

TABLE 9

Skin Sensitisation Test: Induction Phase (Positive Control)

| Animal Number | OBS | Dermal Reactions The Day After Patch Removal | | | | | |
|---|---|---|---|---|---|---|---|
|  |  | 1 | 2 | 3 | 4 | 5 | 6 |
| 21 | ER | 0 | 0 | 0 | 0 | 0 | 0 |
|  | OED | 0 | 0 | 0 | 0 | 0 | 0 |
| 22 | ER | 0 | 0 | 0 | 0 | 0 | 0 |
|  | OED | 0 | 0 | 0 | 0 | 0 | 0 |
| 23 | ER | 0 | 0 | 0 | 0 | 0 | 0 |
|  | OED | 0 | 0 | 0 | 0 | 0 | 0 |
| 24 | ER | 0 | 0 | 0 | 0 | 0 | 0 |
|  | OED | 0 | 0 | 0 | 0 | 0 | 0 |
| 25 | ER | 0 | 0 | 0 | 0 | 0 | 0 |
|  | OED | 0 | 0 | 0 | 0 | 0 | 0 |

TABLE 10

Skin Sensitisation Test: Challenge Phase (Positive Control)

| Animal Number | OBS | Hours After Patch Application | | |
|---|---|---|---|---|
|  |  | 24 | 48 | 72 |
| 21 | ER | 2 | 1 | 1 |
|  | OED | 1 | 1 | 0 |
| 22 | ER | 1 | 1 | 0 |
|  | OED | 1 | 0 | 0 |
| 23 | ER | 0 | 0 | 0 |
|  | OED | 0 | 0 | 0 |
| 24 | ER | 1 | 1 | 0 |
|  | OED | 1 | 0 | 0 |
| 25 | ER | 0 | 0 | 0 |
|  | OED | 0 | 0 | 0 |

ER: ERYTHEMA
OED: OEDEMA

Under the conditions of this test, the estradiol transdermal system would not be considered a sensitizer in the guinea pig. There is no comparative difference of sensitization between the tested estradiol transdermal system and Estraderm control patch.

Skin irritation and sensitization studies for each of the components (i.e. BHT, linoleic acid) of the transdermal delivery system described in this invention, did not show any degree of the irritation and sensitisation.

EXAMPLE 7

Shear Test on Estradiol Transdermal Delivery System

The dosage units derived from the Example 1 are evaluated.

Figure 9:
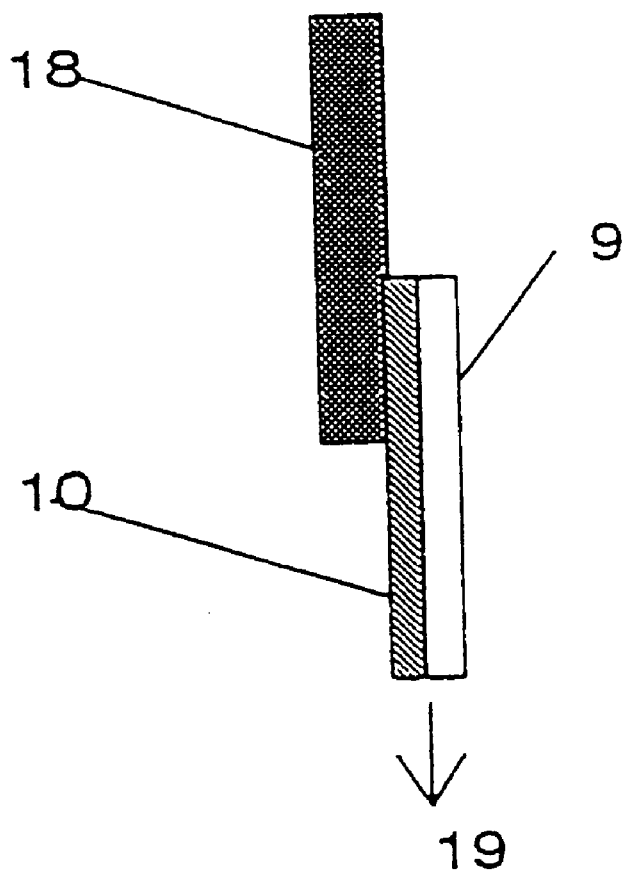
FIG. 9 illustrates a shear test of the present invention.

The adhesiveness of the system introduced by the present invention was evaluated by measuring the cohesive strength of the formulation matrix. A shear test, as illustrated in FIG. 9, is performed according to a standard Test Procedure: A-0150 introduced by Monsanto Chemical Co.

In this test, the patch is attached to a standard steel plate 18 using a controlled pressure, and force 19 is applied to effect "sliding" of the patch from the test plate (adapted from British Pharmacopeia, Vol. II, p. A217, 1993). The results of the test are expressed as the time it takes for the patch to come off the plate, when a given force is applied.

The results of this test are summarized in the following table:

TABLE 11

Adhesion properties of the estradiol transdermal unit

| POSITION | TEST SAMPLE | TIME (sec) | COMMENTS |
|---|---|---|---|
| 7 | E1293A | 398 | Partial transfer of adhesive from the system to the steel plate occured in all cases |
|  |  | 346 |  |
| 8 |  | 261 |  |
|  |  | 392 |  |
|  | Average 342/std. dev. = 57 | | |
| 9 | E1293B | 276 | Partial transfer of adhesive from the system to the steel plate occured in all cases |
|  |  | 281 |  |
| 10 |  | 279 |  |
|  |  | 334 |  |
|  | Average 293/std. dev. = 28 | | |

I claim:

1. A composition for use in a three layer transdermal delivery system, comprising:
   (a) an adhesive matrix having an adhesive strength sufficient to maintain an association between the composition and the skin for at least 3 days in the presence of a non-esterified unsaturated aliphatic acid flux enhancer and an anti-oxidant, wherein the enhancer is linoleic acid; and
   (b) an effective dose of one or more steroid hormones with female sex related activity, the anti-oxidant, flux enhancer and the hormones being contained within the adhesive matrix.

2. The composition according to claim 1, wherein the adhesive matrix is formed from at least one acrylic adhesive.

3. The composition according to claim 2, wherein the adhesive matrix is formed from two acrylic adhesives.

4. The composition according to claim 3, wherein the acrylic adhesives are in a dry weight ratio of about 80% to about 20%.

5. The composition according to claim 4, wherein the hormone is an estrogen.

6. The composition according to claim 5, wherein the estrogen is present in a concentration of about 0.1–8% w/w.

7. The composition according to claim 6, wherein the estrogen is present at about 2% w/w.

8. The composition according to claim 1, wherein the estrogen is selected from the group consisting of 17β estradiol, ethinyl estradiol and combinations thereof.

9. The composition according to claim 1, wherein the flux enhancer is present in a concentration range of 0.1–20% w/w.

10. The composition according to claim 9, wherein the concentration of the flux enhancer is about 5% w/w.

11. The composition according to claim 1, wherein the hormones are estrogen and progestin.

12. The composition according to claim 11, wherein the concentration of progestin is in the range of about 0.1 to about 10% w/w.

13. The composition according to claim 12, wherein the concentration of progestin is 4% w/w.

14. The composition according to claim 11, wherein the progestin is selected from the group consisting of norethindrone acetate, levanorgestrel and medroxyprogesterone.

15. The composition according to claim 1, wherein the anti-oxidant is butylhydroxytoluene (BHT).

16. The composition according to claim 1, wherein the adhesive is comprised of two acrylic adhesives at a dry weight ratio of about 80% to 20%, the adhesive matrix further comprising the hormone, estrogen, the estrogen having a concentration of about 0.1–8% w/w and, optionally, further comprising progestin, at a concentration of about 0.1–10% w/w, the flux enhancer comprising linoleic acid at a concentration of about 0.1–20%, the matrix further containing an antioxidant.

17. The composition according to claim 16, wherein the surface area of the adhesive matrix is less than 5 sq. cm.

18. A transdermal delivery system comprising a composition as claimed in claim 16, wherein a first surface of the adhesive matrix is in contact with a polymeric release liner for sealing and protecting the adhesive during storage, wherein the liner is capable of being removed and discarded prior to use of the transdermal delivery system.

19. A transdermal delivery system according to claim 18, wherein the release liner is selected from the group consisting of a polymeric liner and a paper liner.

20. The transdermal delivery system according to claim 18, wherein a second surface of the adhesive matrix is in contact with a backing layer, the backing layer being substantially impermeable to the components of the composition, the backing layer being occlusive and breathable.

21. The transdermal delivery system according to claim 20, wherein estrogen is delivered in a controlled manner for up to 11 days.

22. The transdermal delivery system according to claim 21, having a surface area of less than 5 sq. cm.

23. A method of administering estrogen through the skin, comprising; selecting a transdermal delivery system according to claim 20, and applying the system to the skin.

24. A method of achieving fertility control in a female subject, comprising (a) applying a transdermal delivery system containing a composition according to claim 1; and (b) permitting controlled release of the hormone into the bloodstream of the patient.

25. A method according to claim 24, wherein the composition in step (a) comprises an adhesive matrix containing estrogen having a concentration of about 0.1–8% w/w and optionally further comprising progestin at a concentration of about 0.1–10% w/w, the flux enhancer comprising linoleic acid at a concentration of about 0.1–20% w/w, and an antioxidant.

26. A method of achieving estrogen replacement in patients deficient in estrogen, comprising:

(a) applying a transdermal delivery system containing a composition according to claim 1; and (b) permitting controlled release of the hormone into the bloodstream of the patient.

27. A method according to claim 26, wherein the composition in step (a) comprises an adhesive matrix containing estrogen having a concentration of about 0.1–8% w/w and optionally further comprising progestin at a concentration of about 0.1–10% w/w, the flux enhancer comprising linoleic acid at a concentration of about 0.1–20% w/w, and an antioxidant.

28. A composition for use in a three layer transdermal delivery system, comprising:

(a) an adhesive matrix in the delivery system having an adhesive strength sufficient to maintain an association between the composition and the skin for at least 3 days in the presence of a flux enhancer and an anti-oxidant, wherein the enhancer is linoleic acid; and (b) an effective dose of one or more steroid hormones with female sex related activity, the flux enhancer and the hormones being contained within the adhesive matrix, wherein the delivery system is capable of maintaining the delivery of a hormone through intact skin at a controlled rate for at least 3 days at a concentration of flux enhancer of no more than 55% w/w.

29. A composition for use in a three layer transdermal drug delivery system, comprising:

(a) an adhesive matrix formed from an acrylate polymer having an adhesive strength sufficient to maintain an association between the composition and skin for at least 3 days in the presence of a linoleic acid flux enhancer and an antioxidant; and (b) a steroid hormone with female sex related activity, the linoleic acid flux enhancer and the hormone being contained within the adhesive matrix.

30. A composition according to claim 29, wherein the flux enhancer has a concentration of no more than about 5% w/w.

* * * * *